(12) United States Patent
Song et al.

(10) Patent No.: US 7,642,067 B2
(45) Date of Patent: Jan. 5, 2010

(54) DEVICE AND METHOD FOR RAPIDLY DETERMINING THE EFFECTIVENESS OF STERILIZATION OR DISINFECTION PROCESSES

(75) Inventors: Kevin Kyung-Hee Song, Tustin, CA (US); Szu-Min Lin, Irvine, CA (US)

(73) Assignee: Ethicon, Inc., Somerville, NJ (US)

( * ) Notice: Subject to any disclaimer, the term of this patent is extended or adjusted under 35 U.S.C. 154(b) by 283 days.

(21) Appl. No.: 11/172,553

(22) Filed: Jun. 30, 2005

(65) Prior Publication Data

US 2007/0003995 A1    Jan. 4, 2007

(51) Int. Cl.
*C12Q 1/22* (2006.01)
*C12N 1/20* (2006.01)
*G01N 33/20* (2006.01)

(52) U.S. Cl. .................. 435/31; 435/252.5; 435/252.7; 436/1; 436/43; 436/80; 424/93.41; 424/93.46

(58) Field of Classification Search .............. 424/93.41, 424/93.46; 435/31, 252.5, 252.7; 436/1, 436/43, 80
See application file for complete search history.

(56) References Cited

U.S. PATENT DOCUMENTS

| | | | |
|---|---|---|---|
| 4,756,882 A | 7/1988 | Jacobs et al. | |
| 5,486,459 A | 1/1996 | Burnham et al. | |
| 5,552,320 A | 9/1996 | Smith | |
| 6,325,972 B1 | 12/2001 | Jacobs et al. | |
| 6,355,448 B1 | 3/2002 | Foltz et al. | |
| 6,365,102 B1 | 4/2002 | Wu et al. | |
| 6,436,659 B1 | 8/2002 | Hui et al. | |
| 6,447,719 B1 | 9/2002 | Agamohamadi et al. | |
| 6,528,277 B1 | 3/2003 | Hendricks et al. | |
| 2003/0064427 A1 | 4/2003 | Felkner et al. | |

FOREIGN PATENT DOCUMENTS

WO    WO 00/66763 A1    11/2000

OTHER PUBLICATIONS

Sasaki et al. 2000. Effect of Calcium in Assay Medium on D Value of *Bacillus stearothermophilus* ATCC 7953 Spores, Applied and Environmental Microbiology, vol. 66, No. 12, pp. 5509-5513.*
EP Search Report dated Oct. 31, 2006.
Warth, A.D.; "Determination of Dipicolinic Acid in Bacterial Spores by Derivative Spectroscopy"; Analytical Biochemistry, 1983, pp. 502-505; vol. 130, No. 2; Academic Press, New York, NY, US.
A. Takahashi, P. Camacho, J. D. Lechleiter, and B. Herman, *Physiological Reviews*, 79, 1089 (1999), Measurement of Intracellular Calcium.
Official Methods of Analysis of AOAC International, 17th Edition, Dr. William Horwitz, vol. 1.
Method 215.1, Atomic Absorption, direct aspiration.
Method 242.1, Atomic Absorption, direct aspiration.
Method 258.1, Atomic Absorption, direct aspiration.
Method 273.1.
Method 243.1.
Method 7703.
Note 40, Detection Limits in Water Using Assorted Sample Introduction Systems.
Method 200.7, Trace Elements in Water, Solids, And Biosolids By Inductively Coupled Plasma-Atomic Emission Spectrometry.
Method 200.8, Determination of Trace Elements in Waters and Wastes By Inductively Coupled Plasma-Mass Spectrometry.
Note #A0009, Analysis of Divalent Transition Metals with Conductivity Detection.
Note #A0012, Simultaneous Analysis of Monovalent & Divalent Cations.
Note 120, Determination of Calcium and Magnesium in Brine.
Bender, Gary R. and Robert E. Marquis, "Spore Heat Resistance and Specific Mineralization", Applied and Environmental Microbiology, Dec. 1985, vol. 50, No. 6, pp. 1414-1421.
"Guide to Reliable pH, Ion and Conductivity Measurements", Radiometer Analytical SAS, catalogue printed on Oct. 14, 2008 from http://www.radiometer-analytica.com/news/en_electrode_catalogue.asp, pp. 1-20.
Designation: D 511—93, "Standard Test Methods for Calcium and Magnesium in Water," American Society for Testing and Materials, pp. 1-9, 1998.
Designation: D 511—93 (Reapproved 1998), "Standard Test Methods for Calcium and Magnesium in Water," American Society for Testing and Materials, pp. 1-6, 2008.
R.T. Wood, "Fundamentals of Thermal Sterilization Processes," in Pharmaceutical Biotechnology—vol. 14: Development and Manufacture of Protein Pharmaceuticals, S.L. Nail and M.J. Akers, eds., 2002 Kluwer Academic/Plenum Publishers, pp. 197-200.

* cited by examiner

*Primary Examiner*—Jon P Weber
*Assistant Examiner*—Kailash C Srivastava

(57) ABSTRACT

A device and a method for rapidly determining the effectiveness of sterilization or disinfection processes are provided. The method involves contacting a biological indicator containing a known number of live spores to a sterilization or disinfection process. When the spores are killed, the minerals in the spores are released. Water is contacted with the dead spores to form an aqueous solution. A parameter related to the concentration of a mineral in the aqueous solution is measured. The effectiveness of the germicidal process is determined from the parameter and the initial number of spores in the biological indicator. Measuring the parameter by measuring the conductivity of the aqueous solution is particularly effective and sensitive.

14 Claims, 3 Drawing Sheets

DEVICE AND METHOD FOR RAPIDLY DETERMINING THE EFFECTIVENESS OF STERILIZATION OR DISINFECTION PROCESSES

FIELD OF THE INVENTION

This invention relates to a device and a method for rapidly determining the effectiveness of a sterilization or disinfection process for medical equipment.

BACKGROUND

Medical devices are sterilized before being used in hospitals, physicians' offices, and other medical facilities. Steam, heat, ethylene oxide, and hydrogen peroxide are commonly used as sterilizing agents.

It is standard practice to include a sterility indicator in a load of articles that are to be sterilized in a sterilizer. The sterility indicator provides a measure of whether the sterilization process was effective in sterilizing the articles in a particular load. If the sterilization process was not effective, as indicated by the sterility indicator, the load of equipment may be rejected for use.

Biological indicators are generally recognized as reliable sterility indicators. The biological indicator includes a carrier that has been inoculated with spores or other microorganisms. Spores are often utilized as indicator organisms in biological indicators, because spores are generally more resistant to sterilization than other microorganisms.

The biological indicator is placed into the sterilizer with the equipment to be sterilized. At the end of the sterilization process, the biological indicator is removed from the sterilizer, and the carrier is immersed in a sterile culture medium. The culture medium and carrier are incubated for a predetermined time at an appropriate temperature. At the end of the incubation period, it is determined whether any microorganisms have grown in the growth medium. If there is no growth of microorganisms in the growth medium, it is assumed that the equipment in the sterilizer has been properly sterilized. If microorganism growth is observed, the sterilization process was not effective, and the articles in the sterilizer may be rejected for use.

The growth of microorganisms may be determined through a signal such as the generation of turbidity in the growth medium or a color change in a pH indicator due to a pH change resulting from byproducts of cell growth in the medium. Biological indicators are described, for example, in Burnham et al. (U.S. Pat. No. 5,552,320) and Hendricks et al. (U.S. Pat. No. 6,436,659), both of which are incorporated herein by reference in their entirety.

Although biological indicators are accurate indicators for the effectiveness of the sterilization cycle, at least 24-48 hours are required to obtain results from the biological indicators. The equipment that was exposed to the sterilization procedure is sometimes kept in quarantine until the results from the biological indicator are available. Medical equipment is expensive, and storage space in medical facilities is limited. Some hospitals therefore use the equipment before the results are available. Storing quarantined medical equipment is not an efficient use of resources. There is a need for a rapid test for determining the effectiveness of a sterilization process.

Foltz et al. (U.S. Pat. No. 6,355,448) describe a method for determining the effectiveness of a sterilization process by measuring the deactivation of enzymes rather than spores. It is stated that the enzyme test procedure requires only a few minutes rather than the several days that are required to obtain results from biological indicators.

The use of a plurality of enzymes rather than a single enzyme was disclosed, for example, by Burnham et al. in U.S. Pat. No. 5,486,459 and Hendricks et al. in U.S. Pat. No. 6,528,277. A plurality of enzymes was believed to better mimic the response of a microorganism to a sterilization process than a single enzyme. Enzymes may react differently than spores or bacteria to the sterilization process, however.

Feltner et al. (U.S. 2003/0064427) describe a method of rapidly determining the effectiveness of a sterilization process by measuring the amount of dipicolinic acid (DPA) that is released during the sterilization process. The spores that are generally used as indicator organisms in sterilization processes contain approximately 10-15 weight % DPA. The DPA is normally present in the cortex and coat of the spore in the form of calcium dipicolinate. Feltner et al. found that DPA was released from the spores when the spores were deactivated.

Feltner et al. determined the concentration of DPA in the solution surrounding the spores through spectroscopic analysis at a wavelength of approximately 545 nm or by derivative ultraviolet spectroscopic analysis. The sensitivity of the analysis could be enhanced by adding a lanthanide salt and by using ultraviolet light for excitation and visible light for emission.

The analysis method of Feltner requires expensive instrumentation and complex data analysis. The detection limit was not given.

There is a need for a method for rapidly measuring the effectiveness of sterilization without expensive instrumentation and complex data analysis methods.

SUMMARY OF THE INVENTION

One aspect of the present invention involves a method for determining the effectiveness of a sterilization or disinfection process. The method includes providing a biological indicator containing an initial known number of live spores, where the live spores contain at least one mineral selected from the group consisting of calcium, manganese, magnesium, potassium, and sodium. The method also includes exposing the biological indicator to a sterilization or disinfection process, thereby killing at least a portion of the live spores, generating a quantity of dead spores.

The method further includes contacting the dead spores with water to generate an aqueous solution containing at least one mineral selected from the group consisting of calcium, manganese, magnesium, potassium, and sodium released from the dead spores, measuring a parameter related to a concentration of at least one mineral in the aqueous solution, where contacting is before measuring. The method also includes determining the effectiveness of the sterilization or disinfection process from the parameter and the initial known number of live spores in the biological indicator.

Advantageously, the parameter is measured with a method selected from the group consisting of atomic absorption, flame emission, ICP, ion chromatography, EDTA titration, complexation titration, spectroscopic analysis of a complex of a fluorescent dye indicator with the at least one ion, and conductivity. Preferably, the parameter is measured by measuring the conductivity of the aqueous solution.

In an embodiment, determining the effectiveness of the sterilization or disinfection process from the parameter includes determining the number of dead spores by comparing the conductivity of the aqueous solution to calibration curves of conductivity versus a number of dead spores and calculating the effectiveness from the number of dead spores and the initial number of live spores. Advantageously, the sterilant or disinfectant is selected from the group consisting of heat, steam, hydrogen peroxide, peracetic acid, ethylene oxide, ozone, chlorine dioxide, ultraviolet light, and radiation.

In an embodiment, the contacting is before the exposing. Advantageously, contacting the dead spores with water includes releasing water from a breakable ampoule by breaking the ampoule. In yet another embodiment, the contacting is after the exposing. Preferably, the initial known number of live spores is at least approximately $1.0 \times 10^6$ spores. Advantageously, the initial known number of live spores is at least approximately $1.0 \times 10^7$ spores. The method may also include culturing spores in a growth medium after measuring and confirming the effectiveness of sterilization or disinfection and determining whether a change occurs in an indicator in the growth medium.

Another aspect of the present invention concerns a biological indicator for determining the effectiveness of a sterilization or disinfection process. The biological indicator includes a known number of live spores, a vial containing the known number of live spores and a breakable ampoule containing distilled water or deionized water. Breaking the ampoule brings the water into contact with the spores in the vial.

The vial may also include a gas-permeable window into the vial, where the gas-permeable window allows sterilant or disinfectant to enter the interior of the vial, contacting the sterilant or disinfectant with the live spores. Preferably, the biological indicator may also include a porous substrate supporting the spores. In yet another embodiment, the biological indicator may also include a second ampoule that contains growth medium.

Another aspect of the present invention concerns a biological indicator that includes a known number of live spores, a vial containing the spores, a breakable ampoule which contains a solution containing water, where breaking the ampoule brings the water into contact with the spores in the vial. The biological indicator also includes probes extending from an exterior of the vial into an interior of the vial, where the probes contact the water in the vial after the ampoule is broken.

Advantageously, the solution containing water is selected from the group consisting of a growth medium, deionized water, and distilled water. Preferably, the probes are electrodes. In an embodiment, the biological indicator also includes a gas-permeable window into the vial, where the gas-permeable window allows sterilant or disinfectant to enter an interior of said vial, thereby contacting the sterilant or disinfectant with the live spores. Preferably, the biological indicator also includes a second ampoule that contains growth medium.

DETAILED DESCRIPTION OF THE INVENTION

Figure 1:
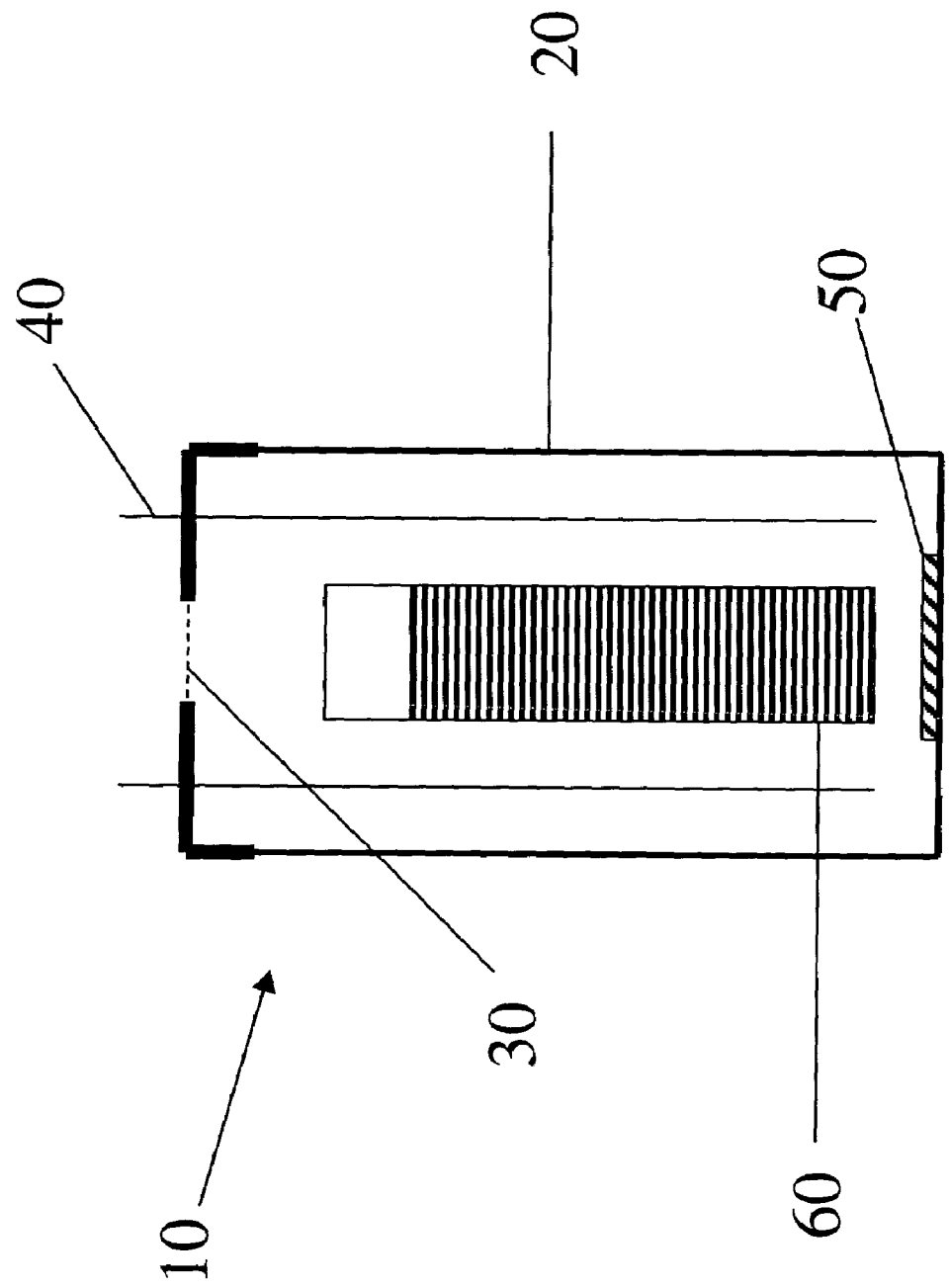
FIG. 1 is a schematic diagram of a conductivity biological indicator with probes according to an embodiment of the present invention.

When medical equipment is sterilized or disinfected in a germicidal process, it is important to be able to rapidly determine whether the germicidal process was effective. As used herein, the term germicidal process includes both sterilization and disinfection.

The embodiments of the present invention provide a device and a method for rapidly determining the effectiveness of a germicidal process. Some of the embodiments of the device and the method may be practiced inside a sterilization apparatus, providing an apparatus and a method for monitoring the effectiveness of a germicidal process while the germicidal process is being performed. Some of the embodiments of the method may be performed quickly, for example, approximately a minute, compared to the 24-48 hours that are required to obtain results from a conventional biological indicator.

Bacterial spores contain minerals such as calcium, manganese, magnesium, potassium and sodium. At least a portion of the minerals may be released from the spores when the spores are deactivated. In an embodiment, the number of spores that are killed during the germicidal process may be determined by measuring a parameter that is related to a concentration of at least one of the minerals that is released into an aqueous solution surrounding the spores in a biological indicator upon death of the spores. The minerals may be calcium, manganese, magnesium, potassium, sodium, or any other suitable mineral.

The number of dead spores in the biological indicator may be determined from the parameter related to the mineral concentration in the solution surrounding the spores. The effectiveness of the germicidal process may be determined by comparing the number of dead spores to the number of live spores that were originally introduced into the biological indicator. In some embodiments, the effectiveness of the germicidal process may be determined at any point in the germicidal process.

After the effectiveness of the germicidal process has been determined, the effectiveness of the germicidical process may be confirmed by culturing the microorganisms or spores in the growth medium in the biological indicator and determining whether growth has occurred by determining a change in a parameter in the growth medium with an indicator, for example a pH indicator or other suitable indicator.

The growth medium may be introduced into the biological indicator after the effectiveness of the sterilization or disinfection process has been determined. In an alternative embodiment, the growth medium may be present in the biological indicator before the effectiveness of the sterilization or disinfection process has been determined.

In an embodiment, the growth medium may be contained in a crushable ampoule in the biological indicator, and the growth medium may be released into the biological indicator by crushing the crushable ampoule. A second crushable ampoule may contain water or an aqueous solution. The water or aqueous solution may be released into the biological indicator by crushing the second ampoule.

The water or aqueous solution in the second crushable ampoule may dissolve the minerals in the dead spores. A parameter related to the mineral concentration in the aqueous solution that may be obtained by dissolving the minerals from the dead spores in the water or aqueous solution released by crushing the second crushable ampoule may be determined. The effectiveness of the sterilization or disinfection process may be determined from the parameter and the initial known number of live spores in the biological indicator.

The effectiveness of the sterilization or disinfection process may be confirmed by determining whether growth of microorganisms or spores occurs when the microorganisms or spores are cultured in the growth medium obtained by crushing the crushable ampoule that contained the growth medium.

Determining whether microorganism or spore growth occurs in the growth medium may confirm the sterilization or disinfection effectiveness results from the parameter related the mineral concentration in the aqueous solution that is obtained by crushing the second crushable ampoule that contains the water or aqueous solution.

Measuring a parameter related to the concentration of a mineral in the aqueous solution in a biological indicator may be performed with a variety of methods, as described in more detail below. Some suitable methods include, but are not limited to, atomic absorption, flame emission, ICP, ion chromatography, EDTA titration, complexation titration, spectroscopic analysis of complex of a fluorescent dye indicator with a mineral ion, and conductivity. Other methods may also be suitable.

Measuring a parameter related to the concentration of minerals in the aqueous solution in a biological indicator may have advantages over measuring the DPA concentration spectroscopically, as taught by Feltner et al. Data analysis with the method of Feltner et al. is complex. The equipment that is used in the analysis is expensive. Further, it would be difficult to perform the DPA analysis inside a sterilization apparatus, because the spectroscopic equipment is bulky and sensitive to chemicals.

Analyzing the data from determining a parameter related to the dissolved mineral concentration in the aqueous solution in a biological indicator according to methods of embodiments of the present invention is generally straightforward. Many of the methods of analyzing the dissolved minerals utilize inexpensive equipment. Some of the analytical methods may be performed inside the sterilization apparatus. Many of the analytical methods may be performed rapidly, within a few minutes. The detection limits for many of the methods are very low.

Although described in the context of sterilization with a combination of hydrogen peroxide and plasma with the STERRAD® process, commercially available from Advanced Sterilization Products of Irvine, Calif., the device and the method according to embodiments of the present invention may be used with a variety of germicidal processes. The description of germicidal processes such as sterilization or disinfection with hydrogen peroxide and plasma through the STERRAD® process is illustrative only and is not meant to be limiting. The device and the method according to embodiments of the present invention may be used with a variety of germicides including, but not limited to, heat, steam, hydrogen peroxide, peracetic acid, ethylene oxide, ozone, chlorine dioxide, ultra-violet light, or radiation, for example, gamma-radiation with or without the use of plasma.

The germicide may be a physical germicide or a chemical germicide. Physical germicides may kill microorganisms through physical methods, for example, heat, steam, ultraviolet light, or radiation. Chemical germicides may kill microorganisms by exposing the microorganisms to a chemical that may be lethal to the microorganism, for example, hydrogen peroxide, peracetic acid, ethylene oxide, ozone, or chlorine. Plasma may be considered to be either a physical or a chemical germicide. Plasma may kill the microorganisms directly, or the plasma may react with a chemical, for example, hydrogen peroxide, to generate an agent that may kill the microorganisms. If the germicide is a chemical, the chemical germicide may be a liquid, a vapor, or a gas.

The STERRAD® process is an exemplary embodiment of a sterilization or disinfection process. The STERRAD® process is described in detail in, for example, U.S. Pat. No. 4,756,882, U.S. Pat. No. 6,325,972, and U.S. Pat. No. 6,365,102, all of which are incorporated herein by reference in their entirety.

The STERRAD® Sterilization Process is performed in the following manner. The items to be sterilized are placed in a sterilization chamber, the chamber is closed, and a vacuum is drawn. An aqueous solution of hydrogen peroxide is injected and vaporized into the chamber so that it surrounds the items to be sterilized. After the pressure in the sterilization chamber is reduced, a low-temperature gas plasma is initiated by applying radio frequency energy to create an electrical field. The hydrogen peroxide vapor is dissociated in the plasma into reactive species that collide, react with, and kill microorganisms. After the activated components react with the organisms or each other, they lose their high energy and recombine to form oxygen, water, and other nontoxic byproducts. The plasma is maintained for a sufficient time to achieve sterilization and remove residuals. At the completion of the process, the RF energy is turned off, the vacuum is released, and the chamber is returned to atmospheric pressure by introducing High Efficiency Particulate-Filtered Air (HEPA) into the chamber. Plasma may also be generated with a low-frequency power source, as described, for example, in U.S. Pat. No. 6,447,719, which is incorporated herein by reference in its entirety.

The device and the method according to embodiments of the present invention are generally not dependent on the form of the germicide that is used in the germicidal process. The embodiments of the device and the method therefore have broad application to a wide range of germicidal processes.

The mineral concentrations in three different organisms are shown in Table 1. The data in Table 1 are from a paper by G. B. Bender and R. E. Marquis, *Applied and Environmental Microbiology* 50, 1414 (1985).

TABLE 1

| Mineral Content of Various Organisms (µmol/mg of dry weight) | | | | | |
|---|---|---|---|---|---|
| Organism | Ca | Mn | Mg | K | Na |
| B. megaterium ATCC19213 | 0.45 | 0.16 | 0.15 | 0.1 | 0.15 |
| B. subtilis niger | 0.42 | 0.99 | 0.3 | 0.28 | 0.18 |
| B. stearothermophilus ATCC7953 | 0.74 | 0.08 | 0.11 | 0.02 | 0.05 |

Dipicolinic acid is about 10% of the dry weight of the organisms.

The dissolved mineral ions in the aqueous solution surrounding the spores in the biological indicator may be measured in a variety of ways. The dissolved minerals may be, for example, calcium, manganese, magnesium, potassium, and sodium, although other minerals may be measured in microorganisms that contain the other minerals.

Detection limits may be provided below for some of the analytical methods for the dissolved mineral ions. The detection limits are believed to be current as of 2005. The detection limits may decrease over time as the instrumentation and methods of analysis improve. The detection limits are not meant to be limiting and are provided only for convenience as a guide for preliminary screening of suitable analytical methods for the dissolved mineral ions.

In an embodiment, at least one of calcium, manganese, magnesium, potassium, and sodium in the aqueous solution in the biological indicator may be analyzed through atomic absorption or flame emission. Analysis through atomic absorption is described, for example, in the Official Methods of AOAC International (2000) 17$^{th}$ Ed. AOAC INTERNATIONAL, Gaithersburg, Md., Official Methods 965.09, 968.08, 085.35. The EPA method of analysis for calcium by atomic absorption is Method 215.1. The corresponding EPA methods for magnesium, potassium, sodium, and manganese are Methods 242.1, 258.1, 273.1, 243.1, respectively. The detection limits that are provided in the EPA methods are 0.01 mg/L for calcium, 0.01 mg/L for manganese, 0.002 mg/L for sodium, 0.001 mg/L for magnesium, and 0.01 mg/L for potassium. The detection limits may change over time.

In an alternative embodiment, at least one of calcium, manganese, magnesium, potassium, or sodium in the aqueous solution may be analyzed through ICP (inductively coupled plasma) analysis. Analysis of calcium, manganese, magnesium, or sodium through ICP analysis may comprise various detection methods. The term ICP as used herein comprises all of the ICP detection methods.

One suitable ICP method is described, for example, in NIOSH Manual of Analytical Methods (NMAM, Fourth Edition, Mar. 15, 2003, Method 7303. The embodiment described in Method 7303 uses the method of inductively coupled argon plasma, atomic emission spectroscopy (ICP-AES), EPA Method 200.7.

ICP-AES is sometimes referred to as ICP-OES, or inductively coupled argon plasma, optical emission spectroscopy. Inductively coupled argon plasma may be abbreviated as ICAP. ICP-AES, ICAP-AES, ICP-OES, and ICAP-OES are different abbreviations for the same method, inductively coupled argon plasma, atomic emission spectroscopy.

Agnes Cosnier et al. provide typical detection limits for various ions in ICP Optical Emission Spectroscopy Application Note 40, Jobin Yvon Inc. of Edison, N.J. Jobin Yvon Inc. is a member of the Horiba Group.

According to Cosnier et al., typical detection limits by EPA 200.7 (ICP-AES) for calcium, magnesium, manganese, sodium, and potassium, respectively, are 30 µg/L, 30 µg/L, 1.4 µg/L, 29 µg/L, and 700 µg/L, respectively.

Other ICP detection methods may be employed in alternative embodiments. For example, mass spectrometry may be used as an ICP detection method. The EPA method for ICP using mass spectrometry as the detection method is Method 200.8, inductively coupled plasma-mass spectrometry or ICP-MS. Manganese is listed as an analyte in Method 200.8 for ICP-MS. According to the Standard Methods Committee for the Examination of Water and Wastewater, magnesium, sodium, and potassium may also be analyzed by ICP-MS, even though they are not specifically listed as analytes in the method. See, for example, www.standardmethods.org.

According to the Research & Productivity Council of Fredericton, NB, Canada, the reporting limits for aqueous samples of calcium, magnesium, manganese, sodium and potassium, respectively, by ICP-MS are 50 µg/L, 10 µg/L, 1 µg/L, 20 µg/L, and 40 µg/L, respectively Other ICP detection methods may be used in other embodiments.

In an alternative embodiment, calcium, magnesium, manganese, sodium or potassium in an aqueous solution may be separated and analyzed through ion chromatography. Suitable ion chromatographic methods are described, for example, in Application Notes #A0009 and A0012 by Alltech Associates, Inc., 2051 Waukegan Road, Deerfield, Ill. 60015-1899 or in Application Note 120 by Dionex Corporation, 1228 Titan Way, Sunnyvale, Calif. 94088-3603.

In yet another embodiment, calcium may be analyzed by EDTA titration, and magnesium may be analyzed through complexation titrimetric methods, as described, for example, in ASTM method D511-93A.

According to the Standard Methods Committee for the Examination of Water and Wastewater, there are interferences with the indicator for determining calcium through EDTA titration when the sample contains phosphorus at levels greater than 50 mg/L. The Committee does not recommend using the EDTA titration method with such samples.

Spores do not normally contain phosphorus levels as high as 50 mg/L. Some biological indicators may comprise a phosphate-based buffer. Biological indicators that comprise phosphate buffers may contain phosphate levels that are greater than 50 mg/L.

In another embodiment, the concentration of calcium or magnesium may be measured through spectroscopic analysis using a fluorescent dye indicator as a probe. The mineral ions calcium, magnesium, sodium, and potassium ions do not naturally fluoresce. The concentrations of the mineral ions may be measured by forming a complex of the ion with a fluorescent indicator molecule. The concentration of the complex of the ion and the fluorescent indicator molecule may be determined through spectroscopic analysis methods, for example, fluorescence spectroscopy.

Tsien and colleagues produced a variety of suitable fluorescent indicators in the 1980's. An article by A. Takahashi, P. Camacho, J. D. Lechleiter, and B. Herman, *Physiological Reviews,* 79, 1089 (1999) provides references to reviews and papers on fluorescent dye indicators, including the indicators of Tsien et al.

Takahashi et al. classifies fluorescent indicators as UV-excitable indicators or visible-excitable indicators. Some examples of UV-excitable indicators include, for example, quin 2, indo 1, fura 2, indo 1FF, fura 2FF, fura PE2, indo PE3, bis-fura 2, $C_{18}$-fura 2, FFT18, and FIP 18. Many of the fluorescent dye indicators have a high affinity for calcium. Mag-indo 1, mag-fura 2, and mag-fura 5 are examples of UV-excitable indicators that have a high affinity for magnesium rather than calcium.

Some visible-wavelength-excitable indicators include, for example, fluo 3, calcium green, Oregon green BAPTA, calcium orange, calcium crimson, fura red, rhod 2, calcium green $C_{18}$, and fura-indoline-$C_{18}$.

The fluorescent indicators may also be classified as nonratiometric indicators or as ratiometric indicators. The excitation and emission wavelengths for nonratiometric indicators are the same whether the indicator is complexed to an ion or not. In contrast, the wavelength of the excitation or emission spectrum of ratiometric indicators shifts when the indicator is complexed with $Ca^{+2}$ or other ion.

Fura 2 is an example of a ratiometric indicator that undergoes a shift in the excitation spectrum when bound to calcium. The excitation maximum for fura 2 is 372 nm when no calcium is present. The excitation maximum shifts to 340 nm when fura 2 is bound to calcium.

The fluorescence emission for fura 2 is at 510 nm whether it is complexed with an ion or not. The excitation maximum, but not the fluorescence emission maximum, shifts when fura 2 is complexed with an ion.

The fluorescence maximum rather than the emission maximum for some ratiometric indicators may shift when the indicator binds to an ion. For example, the ratiometric indicator indo 1 has an emission maximum at 472 nm as a free dye. The emission maximum for indo 1 shifts from 472 nm to 400 nm when indo 1 is complexed with calcium.

There may be advantages to using ratiometric indicators rather than nonratiometric indicators to analyze mineral ions. The ratio of the fluorescence intensity of the ion-bound dye and the ion-free dye for a ratiometric indicator is independent of the concentration of the indicator and the optical path length. Degradation of a ratiometric indicator due to exposure to the excitation source does not affect the ratio of the intensities of the bound dye and the free dye. Determining the concentration of calcium ion or other suitable ion with a ratiometric indicator is independent of the dye loading, cell thickness, dye degradation, excitation source intensity, photobleaching of the dye, detector efficiency, and other variables.

In an embodiment, the concentration of a mineral ion such as calcium, magnesium, potassium, sodium, or manganese in the aqueous solution surrounding the spores in the biological indicator may be determined through spectroscopic determination of a complex of the mineral ion with a fluorescent dye indicator. In an embodiment, the fluorescent dye indicator may be a ratiometric indicator. In an embodiment, the spectroscopic determination of the complex may be performed using fluorescence spectroscopy. Other spectroscopic methods may also be suitable.

In another embodiment, the concentration of mineral ions, for example calcium, magnesium, potassium, sodium, or manganese, may be determined with an ion-sensitive electrode. Ion-sensitive electrodes may be prepared by incorporating an ion-complexing agent into a lipophilic membrane. The membrane in the ion-specific electrode separates a sample solution from a reference solution that contains a known concentration of an ion. The concentration of the ion in the sample solution may be determined from the potential difference between the sample solution and the reference solution by using the Nernst equation.

Calcium-selective electrodes are commercially available, for example, from Fluka and Riedel-de Haën, part of the Sigma-Aldrich family of companies, as Calcium Ionophore Selectophore®, from Thermo Electron Corporation as Orion Ion-Plus® calcium electrodes, or from Radiometer Analytical SAS as ISE25Ca. Other calcium-selective electrodes may also be suitable.

Similar ion-specific electrodes are commercially available for other ions.

As noted in the article by Takahashi, et al., the range of calcium concentrations that may be measured with calcium-selective electrodes is wider than the range of calcium concentrations that can be measured with fluorescent dye indicators. The pCa for calcium-selective electrodes is pCa 9 to pCa 1, compared to pCa 7.5 to pCa 5 for, for example, indo 1 fluorescent dye. According to the Radiometer Analytical SAS catalog, available at www.radiometer-analytical.com, the Radiometer Analytical ISE25Ca electrode has a range of $10^{-6}$ to $10^0$ M Ca. Other calcium-specific electrodes may have different ranges. It is stated in Takahashi, et al. that the response time of calcium-selective electrodes is slower than the response time of fluorescent indicators, however.

In an exemplary embodiment, the concentration of dissolved minerals, for example calcium, magnesium, potassium, sodium, or manganese, may be determined by measuring the conductivity of an aqueous solution surrounding the spores in a biological indicator. Ions such as calcium, magnesium, potassium, sodium, or manganese conduct electricity. The conductivity of the aqueous solution increases as the concentration of dissolved mineral ions increases.

In an embodiment, aqueous solutions containing varying concentrations of ions may be prepared, the conductivities of the solutions may be measured, and calibration curves of ion concentration versus conductivity may be prepared. The concentrations of ions in aqueous solutions may then be determined by measuring the conductivity of the solution and relating the conductivity of the aqueous solution to the concentration of the ions using the calibration curve of ion concentration versus conductivity.

In another embodiment, calibration curves of the number of dead spores versus conductivity may be generated, as shown in Example 1 below. The number of dead spores in the aqueous solution in the biological indicator may be determined, for example, by measuring the conductivity of the aqueous solution that surrounds the spores in a biological indicator and relating the conductivity to the number of dead spores through the calibration curves.

The conductivity of the solution may be measured, for example, with a conductivity meter. Other instruments for measuring the conductivity of the solution are also suitable.

Biological Indicator

An example of a suitable apparatus or device for determining the conductivity of an aqueous solution in a biological indicator is shown in FIG. 1. The apparatus or kit of FIG. 1 is only one form of an apparatus that may be used for determining the conductivity. Other forms of apparatus for determining the conductivity may also be suitable.

As shown in FIG. 1, a conductivity biological indicator 10 may comprise vial 20 having gas-permeable window 30. In an embodiment, gas-permeable window 30 may comprise a material that is permeable to germicide, for example, TYVEK®, a trademark registered to DuPont for spun polyethylene. Other gas permeable membranes may also be suitable. In other embodiments, gas-permeable window 30 may comprise an uncovered opening in vial 20. In another embodiment, gas-permeable window 30 may comprise a pinhole, an opening small enough that liquid may not leak out of the biological indicator 10. When radiation or ultraviolet light is used as a sterilizing agent or disinfecting agent, the biological indicator 10 may not comprise a gas-permeable window 30. In an embodiment, vial 20 may comprise a cap to completely close the vial.

Probes 40 extend from an exterior of vial 20 into an interior of vial 20. Vial 20 contains an initial number of spores 50. The probes 40 may generally comprise a conductive metal, for example platinum or copper. The probe 40 may comprise, for example a wire, plate, or bar. A portion of the probe 40 may be coated with a protective coating, for example, plastic. The protective coating may decrease an amount of reaction of the germicide with the probe 40. The probes 40 may comprise electrodes.

The initial number of spores 50 may be determined by standard methods known to those skilled in the art. The spores 50 may be any suitable spores. The spores of Table 1, *B. megaterium, B. subtilis niger*, and *B. stearothermophilus* may be suitable. The spores 50 may comprise, for example, at least one mineral selected from the group consisting of calcium, manganese, magnesium, potassium, and sodium. Other spores may comprise other minerals.

In an embodiment, the spores 50 may be in a form of dried spores. In an alternative embodiment, the spores 50 may be supported on a porous substrate, for example, a porous glass disk.

Conductivity biological indicator 10 comprises crushable ampoule 60. Crushable ampoule 60 may be made of a frangible material, for example, glass. Crushable ampoule 60 contains an aqueous solution. Crushable ampoule 60 may be any breakable enclosure that allows the aqueous solution to escape the crushable ampoule 60 when the crushable ampoule is crushed. The aqueous solution may comprise any suitable aqueous solution, for example, deionized water, distilled water, or a growth medium for the spores 50. In other embodiments, the aqueous solution may comprise a chemical that reacts with the mineral ion or an aqueous solution that does not contain the mineral that is to be detected. In an embodiment, the biological indicator 10 may further comprise a second crushable ampoule (not shown) that contains growth medium.

The gas-permeable window 30 is shown at the top of vial 20 in FIG. 1. Other locations in the vial 20 are also suitable.

In an embodiment, vial 20 may be made of a deformable material, for example, polypropylene.

Alternative Embodiment of a Biological Indicator

Figure 2:
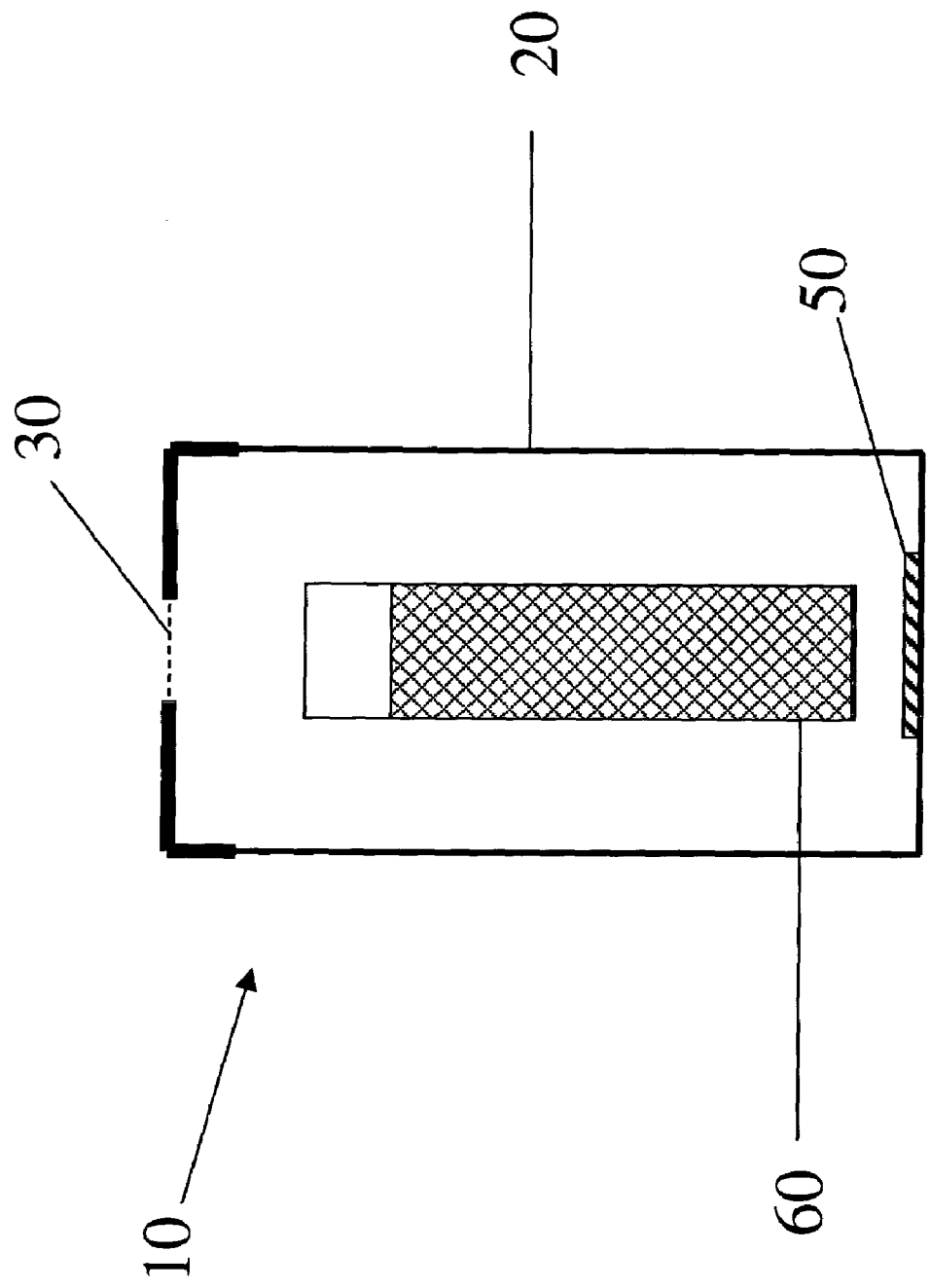
FIG. 2 is a schematic diagram of a conductivity biological indicator without probes according to an embodiment of the present invention.

FIG. 2 shows an alternative embodiment of a biological indicator 10. The embodiment of the biological indicator 10 of FIG. 2 is similar to the embodiment of the conductivity biological indicator 10 of FIG. 1. Unlike the embodiment shown in FIG. 1, the biological indicator of FIG. 2 does not comprise probes 40. The parameter related to the concentration of minerals may be determined with a variety of methods. The crushable ampoule 60 of the biological indicator 10 of FIG. 2 contains water, for example deionized water or distilled water. In other embodiments, the aqueous solution may comprise a chemical that reacts with the mineral ion or an aqueous solution that does not contain the mineral that is to be detected. The water in the crushable ampoule 60 of the embodiment of the biological indicator 10 shown in FIG. 2 does not support the growth of microorganisms.

The biological indicator of FIG. 2 may further comprise a second crushable ampoule (not shown) containing growth medium.

Method of Determining the Completeness of a Germicidal Treatment Utilizing the Conductivity Biological Indicator of FIG. 1

The conductivity biological indicator 10 shown in FIG. 1 may be placed in a sterilization apparatus, and a germicidal cycle may be run. Germicide may enter vial 20 through gas-permeable window 30 during the germicidal cycle. The germicide may contact the spores 50, thereby killing at least a portion of the spores 50 enclosed in vial 20.

After the germicidal cycle is complete, the aqueous solution that is contained in crushable ampoule 60 may be released by crushing the crushable ampoule 60. Crushable ampoule 60 may be crushed in any suitable manner. For example, vial 20 may be deformed. If the vial 20 is deformed, the walls of the vial 20 may contact the crushable ampoule 60, crushing the crushable ampoule 60.

Crushing crushable ampoule 60 releases the aqueous solution that is contained in the crushable ampoule. The aqueous solution may contact the spores 50 in vial 20. Contacting the spores 50 with the aqueous solution contained in crushable ampoule 60 may dissolve the minerals that were contained in the spores, forming an aqueous solution comprising the minerals. The aqueous solution of the dissolved minerals may contact probes 40.

A conductivity meter or other suitable device for measuring conductivity may be connected to probes 40 to measure the conductivity of the aqueous solution in vial 20. As shown in Table 2 and FIG. 2 of Example 1, the conductivity of the water enclosed in vial 20 increases as the number of dead spores in the vial 20 increases. The increased conductivity of the aqueous solution may be related to the increased concentration of dissolved minerals, for example calcium, magnesium, sodium, or potassium, which are released from the spores when the spores are killed with the germicide.

The increased conductivity of the water in vial 20 may be correlated with the effectiveness of the germicidal treatment by comparing the number of dead spores, determined from the conductivity of the aqueous solution in the conductivity biological indicator 10, with the initial number of live spores in the conductivity biological indicator 10.

Wires (not shown), may be connected to the probes 40 on the self-contained biological indicator 10 to transmit the conductivity of the aqueous solution enclosed in the vial 20 to a conductivity meter or other suitable device for measuring the conductivity of the aqueous solution. In an embodiment, the wires may pass through the walls of the sterilization apparatus so that the conductivity results may be measured outside of the sterilization apparatus while the germicidal treatment is being performed or after the germicidal process is complete. The conductivity results with the conductivity biological indicator of FIG. 1 may be measured either inside or outside of a sterilization or germicidal treatment apparatus.

Method of Determining the Completeness of a Germicidal Treatment Utilizing the Biological Indicator of FIG. 2

A method of determining the completeness of a germicidal treatment with the biological indicator 10 of FIG. 2 is generally similar to the method for the conductivity biological indicator 10 of FIG. 1. The biological indicator 10 of FIG. 2 may be placed in a sterilization apparatus or germicidal treatment apparatus, and a germicidal cycle may be run. Germicide may enter vial 20 through gas-permeable window 30 during the germicidal cycle. The germicide may contact the spores 50, thereby killing at least a portion of the spores 50 enclosed in vial 20. Killing the spores 50 may release the minerals that are contained in the spores 50.

After the germicidal cycle is complete, the water contained in crushable ampoule 60 may be released by crushing the crushable ampoule 60. Crushable ampoule 60 may be crushed in any suitable manner. For example, vial 20 may be deformed. Deforming the vial 20 may contact the walls of the vial 20 with the crushable ampoule 60, crushing the crushable ampoule 60. The crushable ampoule 60 of the embodiment of the biological indicator 10 of FIG. 2 may be crushed inside the sterilization apparatus or germicidal treatment apparatus or may be crushed outside the apparatus.

Crushing crushable ampoule 60 releases the water that is contained in the crushable ampoule. The water may contact the spores 50 contained in vial 20. Contacting the spores 50 with the water contained in crushable ampoule 60 may dissolve the minerals that were contained in the spores, forming an aqueous solution comprising the minerals that were released when the spores 50 in the vial 20 were killed. The minerals in the aqueous solution may be detected by any suitable method. Determination by conductivity is described to illustrate the method.

Probes (not shown) may be inserted into the aqueous solution comprising dissolved minerals in vial 20. The conductivity of the aqueous solution in the vial 20 may be determined with any suitable measuring device, for example, a conductivity meter. The determination of conductivity of the conductivity biological indicator 10 of FIG. 2 is performed outside of the sterilization apparatus or germicidal apparatus, because the probes are inserted into the vial outside of the apparatus.

The probes may be inserted, for example, through the gas permeable window 30. Alternatively, a portion of the vial 20 may be removed, at least temporally, in order to insert probes into the aqueous solution in the vial 20 of the conductivity biological indicator 10 of FIG. 2.

The effectiveness of the germicidal treatment may be determined from the conductivity of the aqueous solution in the vial 20 of the conductivity biological indicator 10 of FIG. 2 in a manner similar to the method previously described for the conductivity biological indicator 10 of FIG. 1.

The cost of a conductivity meter is very low. The cost of instruments such as the derivative ultraviolet spectrometer of Felkner et al. is very high. Measuring the conductivity of a solution is very rapid, less than a minute, far faster than the 1-2 days required to obtain sterilization results from biological indicators.

As shown in the data in Table 2 and FIG. 2 of Example 1, the conductivity of the aqueous solution is very sensitive to the number of dead spores. The conductivity increases from 1.15 µS/cm when $8.2 \times 10^6$ dead spores are present to 3.36 µS/cm when $8.2 \times 10^7$ dead spores are present. The 2 µS/cm change in conductivity when going from $8.2 \times 10^6$ dead spores to $8.2 \times 10^7$ dead spores is readily distinguishable. The conductivity of the aqueous solution in the biological indicator changes significantly as the number of dead spores increase.

The deionized water that was used in Example 1 had a conductivity of 0.90 µS/cm. The total conductivities that were measured in Example 1 ranged from 0.90 µS/cm for a sample containing $1.6 \times 10^4$ dead spores to 50.10 µS/cm for a sample containing $1.6 \times 10^9$ dead spores. The conductivity of a sample containing $8.2 \times 10^4$ or fewer spores has the same conductivity as deionized water.

The conductivity of the water may be lowered through methods such as reverse osmosis. Lowering the conductivity of the water that is used in the conductivity biological indicator would reduce the "noise" in the conductivity determination, thereby increasing the sensitivity of determining the number of dead spores in a biological indicator through conductivity measurements.

As previously described, the parameter related to the concentration of the mineral ions in the aqueous solution in a biological indicator may be determined by a wide variety of methods. An embodiment of determining a conductivity of the aqueous solution contained in the biological indicator is an exemplary embodiment. Other methods for determining the parameter related to the concentration of mineral ions in the aqueous solution may also be suitable.

The following examples are meant to be illustrative only and are not meant to be limiting on the scope.

EXAMPLES

Example 1

Determination of Conductivity Versus Number of Spores

The conductivity of aqueous solutions containing various populations of live *B. stearothermophilus* spores was determined. The conductivity of the aqueous solution was approximately 0.89 µS/cm, regardless of the live spore population. Sterile deionized water also had a conductivity of 0.89 µS/cm. Live spores therefore do not have any significant impact on the conductivity of the aqueous solution. The conductivity due to the live spores and deionized water is reported as 0.90 µS/cm in all of the examples in Table 2 below.

Figure 3:
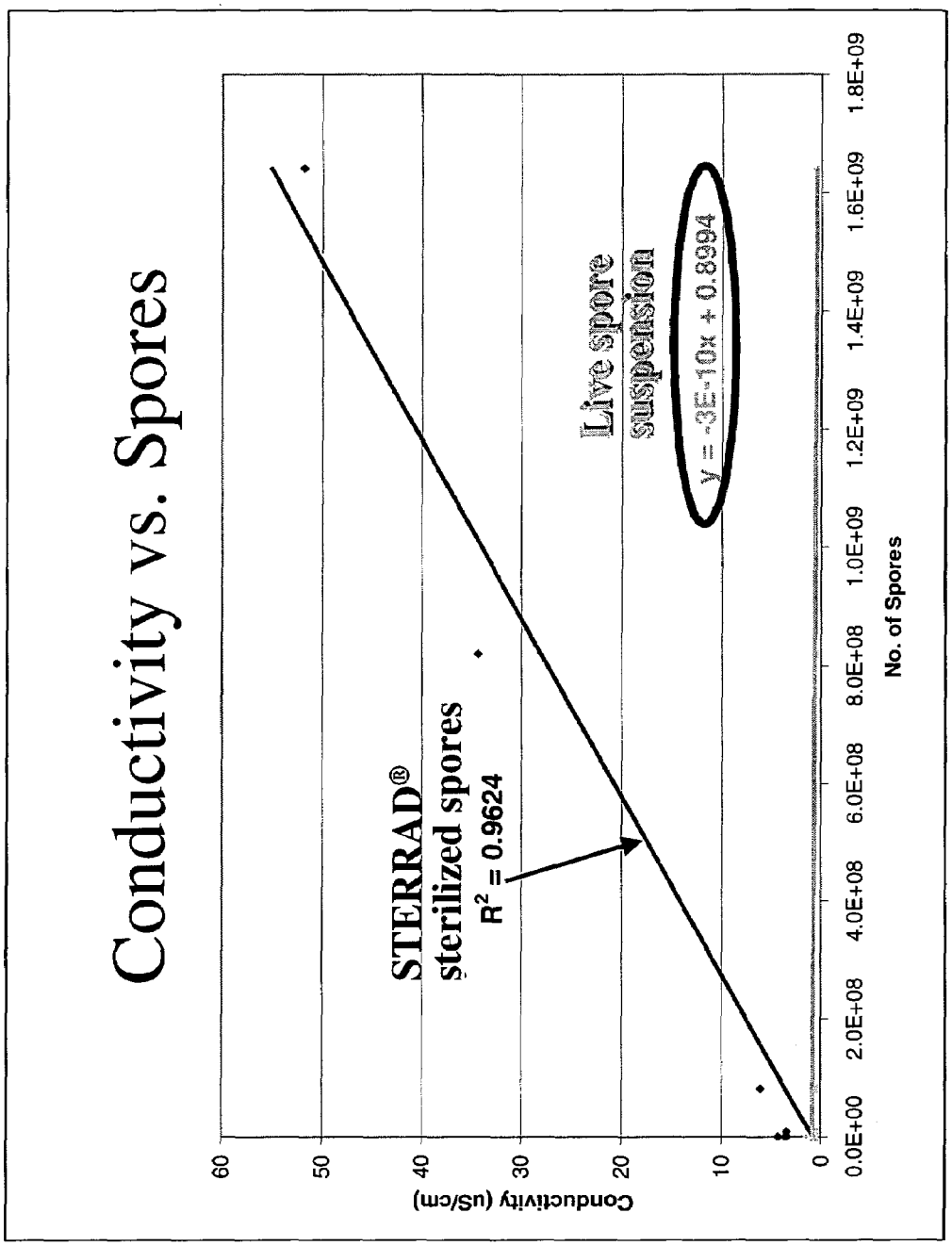
FIG. 3 is a plot of conductivity in $\mu$S/cm versus a number of dead spores.

Varying numbers of *B. stearothermophilus* spores were placed onto porous glass substrates. The substrates and spores were treated with hydrogen peroxide/plasma in a Sterrad® 100S Sterilizer, commercially available from Advanced Sterilization Systems, Irvine, Calif. All of the spores on the porous glass substrates were killed under the conditions of the experiments. Deionized water was added to the glass substrate, and the conductivities of the solutions were determined. The results are shown in Table 2 below. FIG. 3 shows the data graphically as a plot of conductivity versus number of dead spores.

TABLE 2

Solution Conductivity Versus Number of Dead Spores

| | Conductivity (µS/cm) | |
|---|---|---|
| Number of Spores | Live Spores and DI | Dead Spores After Exposure |
| $1.6 \times 10^9$ | 0.90 | 50.10 |
| $8.2 \times 10^8$ | 0.90 | 25.50 |
| $8.2 \times 10^7$ | 0.90 | 3.36 |
| $8.2 \times 10^6$ | 0.90 | 1.15 |
| $8.2 \times 10^5$ | 0.90 | 0.92 |
| $8.2 \times 10^4$ | 0.90 | 0.90 |
| $1.6 \times 10^4$ | 0.90 | 0.90 |

The conductivity of an aqueous suspension containing $8.2 \times 10^6$ dead spores was 1.15 µS/cm, while the conductivity of an aqueous suspension containing $1.6 \times 10^9$ dead spores was 50.10 µS/cm. An aqueous suspension containing $8.2 \times 10^6$ dead spores is therefore readily differentiable from a suspension having $1.6 \times 10^9$ dead spores.

An aqueous suspension containing $8.2 \times 10^5$ dead spores has a conductivity of 0.92 µS/cm, not distinguishable from the conductivity of 0.90 µS/cm for a suspension of $8.2 \times 10^4$ dead spores.

As shown by the data in Table 2, a conductivity of 1.15 µS/cm after sterilization indicates that at least $8.2 \times 10^6$ spores were killed during the sterilization. In an embodiment, at least approximately $1.0 \times 10^6$ spores are utilized in the biological indicator. A conductivity of approximately 1.15 µS/cm in the aqueous solution after sterilization would indicate that at least $8.2 \times 10^6$ spores were killed.

Utilizing a larger number of live spores in the biological indicator may provide an even higher degree of assurance that effective sterilization has been achieved when the conductivity of the aqueous solution in the conductivity biological indicator is at least 1.15 µS/cm. In an embodiment, the initial number of live spores in the conductivity biological indicator may be at least approximately $1.0 \times 10^7$ live spores. Using a larger number of live spores provides even greater assurance that the germicidal treatment has been effective.

Lower conductivity values than the conductivity values shown in Table 2 could be measured, if water having lower conductivity were used to prepare the aqueous solution that was added to the dead spores in the biological indicator. Water having lower conductivity can be prepared, for example, by using reverse osmosis.

Various modifications and alterations of this invention will be apparent to those skilled in the art without departing from the scope and spirit of this invention. It is to be understood that the invention is not limited to the embodiments disclosed therein, and that the claims should be interpreted as broadly as the prior art allows.

What is claimed is:

1. A method for determining the effectiveness of a sterilization or disinfection process, said method comprising:
    providing a biological indicator comprising an initial known number of live bacterial spores, said known number of said live spores comprising at least one mineral selected from the group consisting of calcium, manganese, magnesium, potassium, and sodium;

exposing said biological indicator to a sterilization or disinfection process, thereby killing at least a portion of said known number of live spores, thereby generating a quantity of dead spores;

contacting the dead spores with water to generate an aqueous solution comprising at least one mineral selected from the group consisting of calcium, manganese, magnesium, potassium, and sodium released from the dead spores;

measuring a parameter related to a concentration of at least one mineral released from the dead spores selected from the group consisting of calcium, manganese, magnesium, potassium, and sodium in the aqueous solution, wherein the contacting is before the measuring; and determining the effectiveness of the sterilization or disinfection process from the parameter and the initial known number of live spores in said biological indicator.

2. The method of claim 1, wherein said parameter related to a concentration of at least one ion selected from the group consisting of calcium, manganese, magnesium, potassium, and sodium in said aqueous solution is measured with a method selected from the group consisting of atomic absorption, flame emission, ICP, ion chromatography, EDTA titration, complexation titration, spectroscopic analysis of a complex of a fluorescent dye indicator with the at least one ion, and conductivity.

3. The method of claim 1, wherein said parameter related to a concentration of at least one ion selected from the group consisting of calcium, manganese, magnesium, potassium, and sodium in said aqueous solution is measured by measuring a conductivity of said aqueous solution.

4. The method of claim 3, wherein determining the effectiveness of the sterilization or disinfection process from the parameter comprises determining the number of dead spores by comparing the conductivity of said aqueous solution to calibration curves of conductivity versus a number of dead spores and calculating the effectiveness from the number of dead spores and the initial number of live spores.

5. The method of claim 1, wherein the sterilant or disinfectant is selected from the group consisting of heat, steam, hydrogen peroxide, peracetic acid, ethylene oxide, ozone, chlorine dioxide, ultraviolet light, and radiation.

6. The method of claim 1, wherein the contacting is before the exposing.

7. The method of claim 1, wherein contacting the dead spores with water comprises releasing water from a breakable ampoule by breaking the ampoule.

8. The method of claim 1, wherein the contacting is after the exposing.

9. The method of claim 1, wherein the initial known number of live spores is at least approximately $1.0 \times 10^6$ spores.

10. The method of claim 1, wherein the initial known number of live spores is at least approximately $1.0 \times 10^7$ spores.

11. The method of claim 1, further comprising culturing spores in a growth medium after said measuring and confirming an effectiveness of sterilization or disinfection by determining whether a change occurs in an indicator in the growth medium.

12. A method for determining the effectiveness of a sterilization or disinfection process, said method comprising:

exposing a biological indicator comprising an initial known number of live bacterial spores to a sterilization or disinfection process, said known number of said live spores comprising at least one mineral selected from the group consisting of calcium, manganese, magnesium, potassium, and sodium, said exposing thereby killing at least a portion of said known number of live spores and producing a quantity of dead spores;

generating an aqueous solution comprising at least one mineral selected from the group consisting of calcium, manganese, magnesium, potassium, and sodium released from said dead spores;

measuring a parameter related to a concentration of at least one mineral released from the dead spores selected from the group consisting of calcium, manganese, magnesium, potassium, and sodium in the aqueous solution, wherein the generating is before the measuring; and determining the effectiveness of the sterilization or disinfection process from the parameter and the initial known number of live spores in said biological indicator.

13. A method for determining the effectiveness of a sterilization or disinfection process, the method comprising:

providing a biological indicator comprising an initial known number of live bacterial spores, the known number of said live bacterial spores comprising at least one mineral selected from the group consisting of calcium, manganese, magnesium, potassium, and sodium;

exposing the biological indicator to a sterilization or disinfection process, thereby killing at least a portion of the known number of live spores, thereby generating a quantity of dead spores that release at least a portion of the at least one mineral when the spores are killed;

contacting the dead spores with deionized or distilled water to generate an aqueous solution comprising at least one mineral selected from the group consisting of calcium, manganese, magnesium, potassium, and sodium released from the dead spores;

measuring a parameter related to a concentration of the at least one mineral in the aqueous solution and released from the dead spores, the mineral selected from the group consisting of calcium, manganese, magnesium, potassium, and sodium, wherein the contacting is before the measuring; and determining the effectiveness of the sterilization or disinfection process from the parameter and the initial known number of live spores in the biological indicator.

14. The method of claim 13, wherein contacting the dead spores with deionized or distilled water comprises releasing deionized or distilled water from a breakable ampoule by breaking the ampoule.

* * * * *